(12) United States Patent
Ballin et al.

(10) Patent No.: US 6,675,974 B2
(45) Date of Patent: Jan. 13, 2004

(54) DEVICE FOR HANDLING SPECIMENS

(75) Inventors: Benny Ballin, Ganey Tikva (IL); Amir Geron, Givataim (IL); Anat Weinstein, Haifa (IL); Nir Barkai, Omer (IL)

(73) Assignee: Trek Diagnostic Systems Inc., Westlake, OH (US)

( * ) Notice: Subject to any disclaimer, the term of this patent is extended or adjusted under 35 U.S.C. 154(b) by 49 days.

(21) Appl. No.: 10/010,241

(22) Filed: Nov. 8, 2001

(65) Prior Publication Data

US 2002/0041834 A1 Apr. 11, 2002

Related U.S. Application Data

(62) Division of application No. 09/180,356, filed as application No. PCT/IL97/00141 on May 1, 1997, now Pat. No. 6,350,414.

(30) Foreign Application Priority Data

May 6, 1996 (IL) .................................................. 118155

(51) Int. Cl.⁷ ............................................. B01D 35/00
(52) U.S. Cl. ...................... 210/477; 210/451; 210/473; 422/101; 422/102
(58) Field of Search ............................. 210/406, 416.1, 210/451, 473, 477; 422/101, 102; 435/288.3, 288.4, 288.5

(56) References Cited

U.S. PATENT DOCUMENTS

| | | | |
|---|---|---|---|
| 3,876,377 A | 4/1975 | Cinqualbre | 23/253 |
| 3,888,770 A | 6/1975 | Avital et al. | 210/238 |
| 3,963,355 A | 6/1976 | Aldridge et al. | 356/201 |
| 3,966,606 A | 6/1976 | Ahmad | 210/136 |
| 4,235,964 A | 11/1980 | Bochner | 435/34 |
| 4,493,815 A | 1/1985 | Fernwood et al. | 422/101 |
| 4,746,631 A | 5/1988 | Clagett | 436/518 |
| 4,806,316 A | 2/1989 | Johnson et al. | 422/100 |
| 4,902,624 A | 2/1990 | Columbus et al. | 435/316 |
| 5,047,215 A | 9/1991 | Manns | 422/101 |
| 5,123,937 A | 6/1992 | Shibata et al. | 55/16 |
| 5,190,666 A | 3/1993 | Bisconte | 210/744 |
| 5,223,133 A | 6/1993 | Clark et al. | 210/232 |
| 5,227,137 A | 7/1993 | Monti et al. | |
| 5,306,420 A | 4/1994 | Bisconte | 210/143 |
| 5,589,350 A | 12/1996 | Bochner | 435/29 |

FOREIGN PATENT DOCUMENTS

| | | |
|---|---|---|
| EP | 0532762 | 3/1993 |
| WO | 9411489 | 5/1994 |

*Primary Examiner*—John Kim
(74) *Attorney, Agent, or Firm*—Jones Day

(57) ABSTRACT

An apparatus for use with an array of liquid specimen containers having open upper ends includes a panel structure having an array of openings corresponding to the array of liquid specimen containers such that the open upper ends of the containers will be aligned with the openings upon placement of the panel structure over the containers in an upright engagement with the containers. The apparatus further includes filter material stretched across the openings so as to extend across the open upper ends of the containers in overlying abutment with the open upper ends of the containers when the panel structure is in the upright engagement. In this arrangement, liquid contents of the containers can flow downward through the filter material when the panel structure and the containers are together moved from their upright engagement to an overturned engagement inverted from their upright engagement.

20 Claims, 13 Drawing Sheets

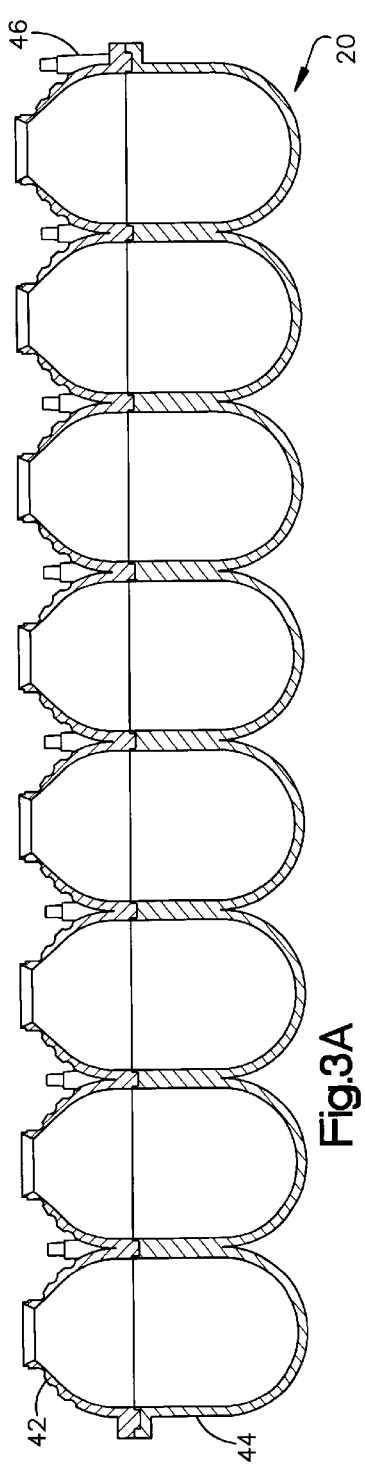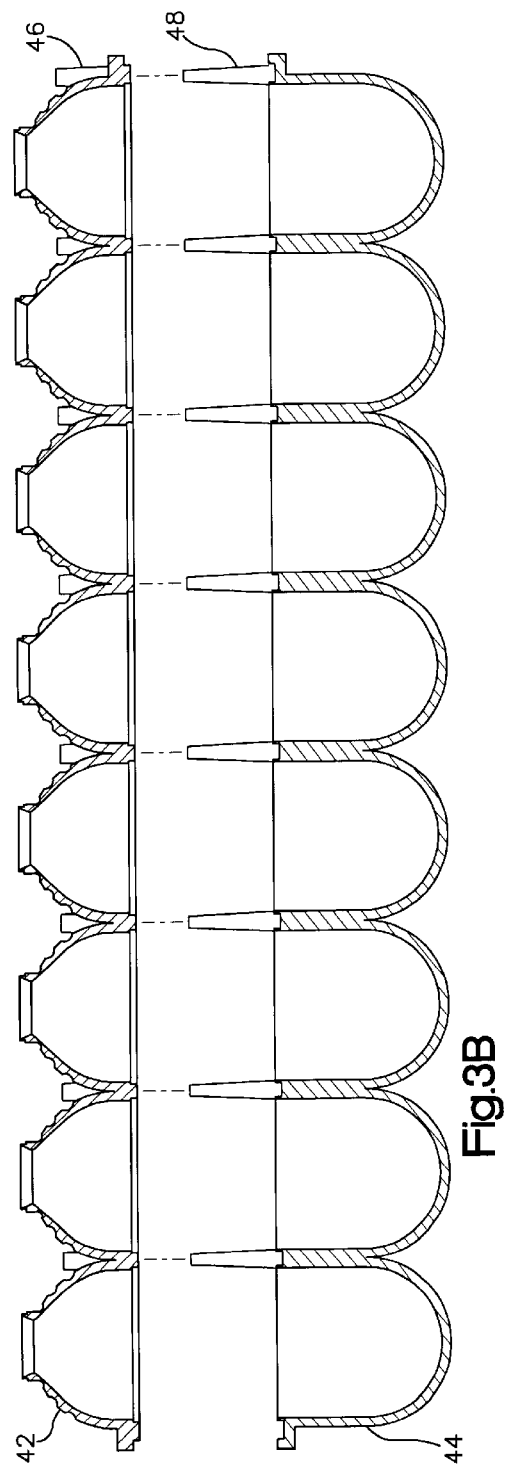

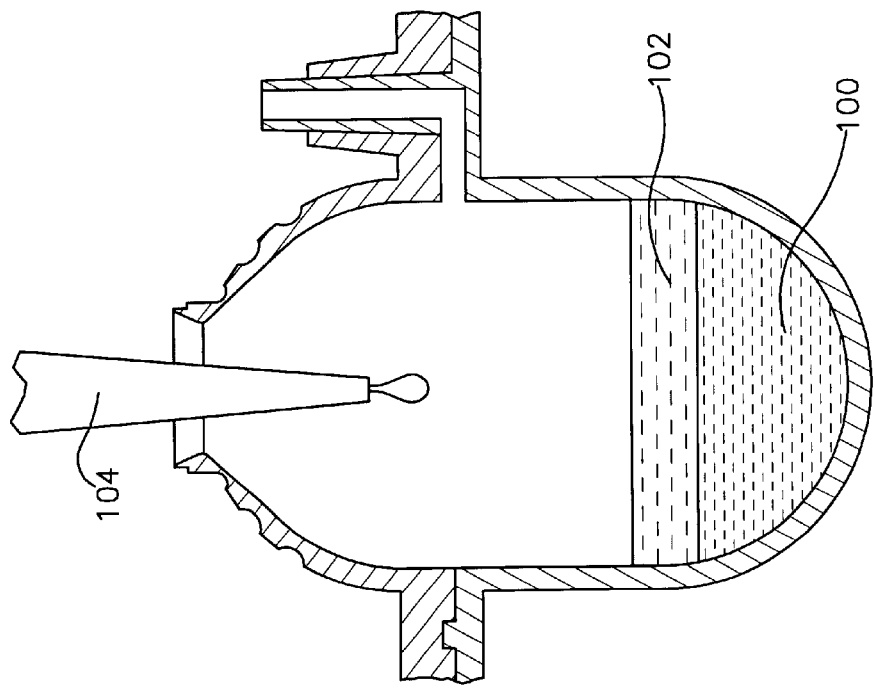
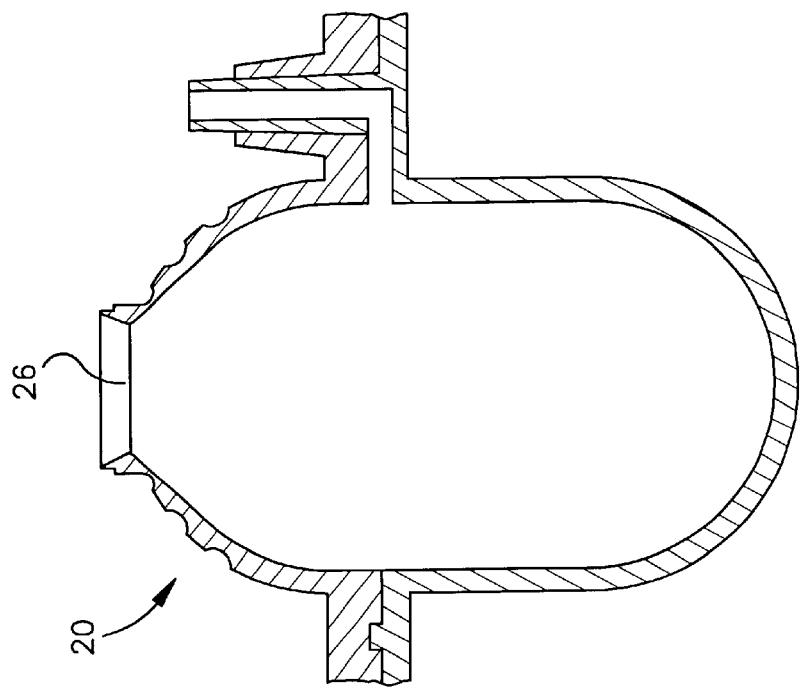

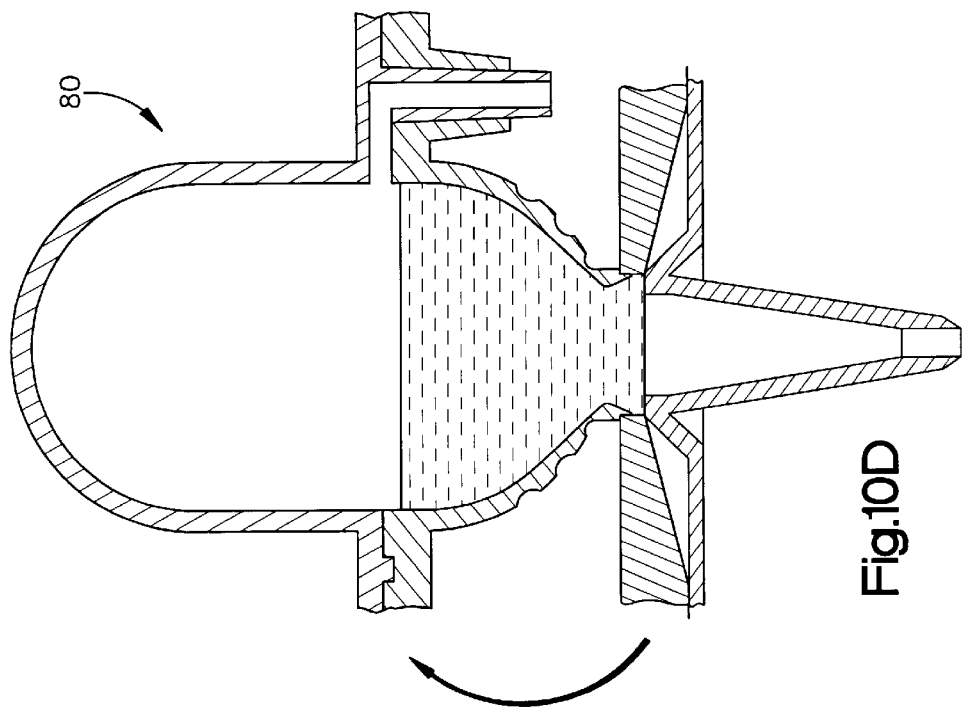
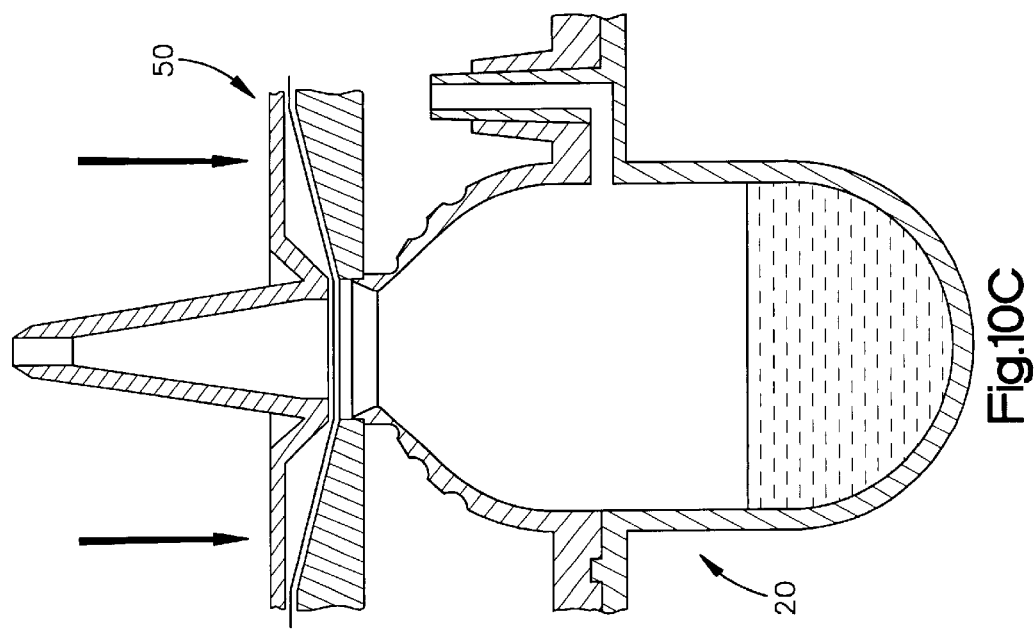
Fig.10D
Fig.10C

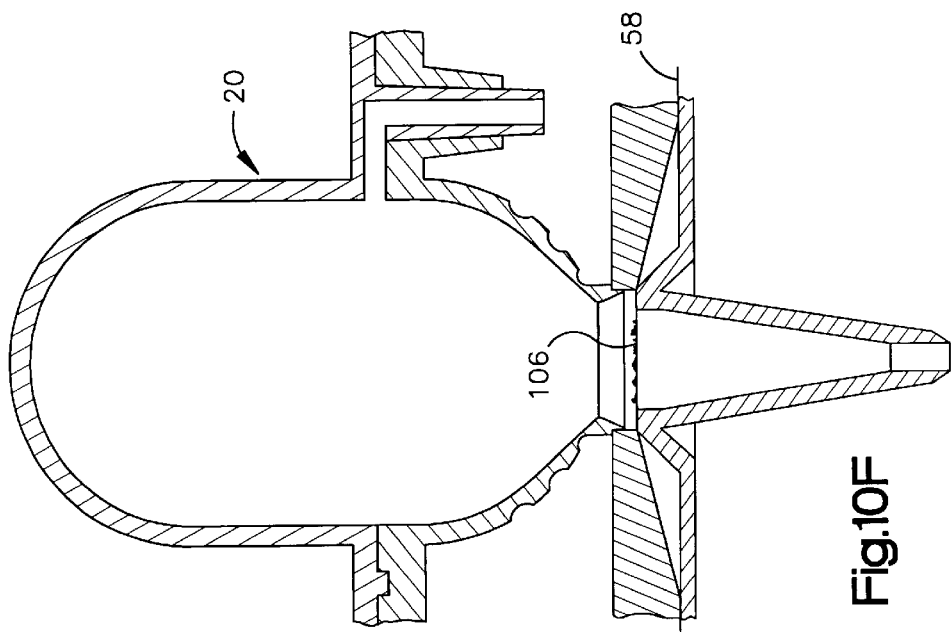
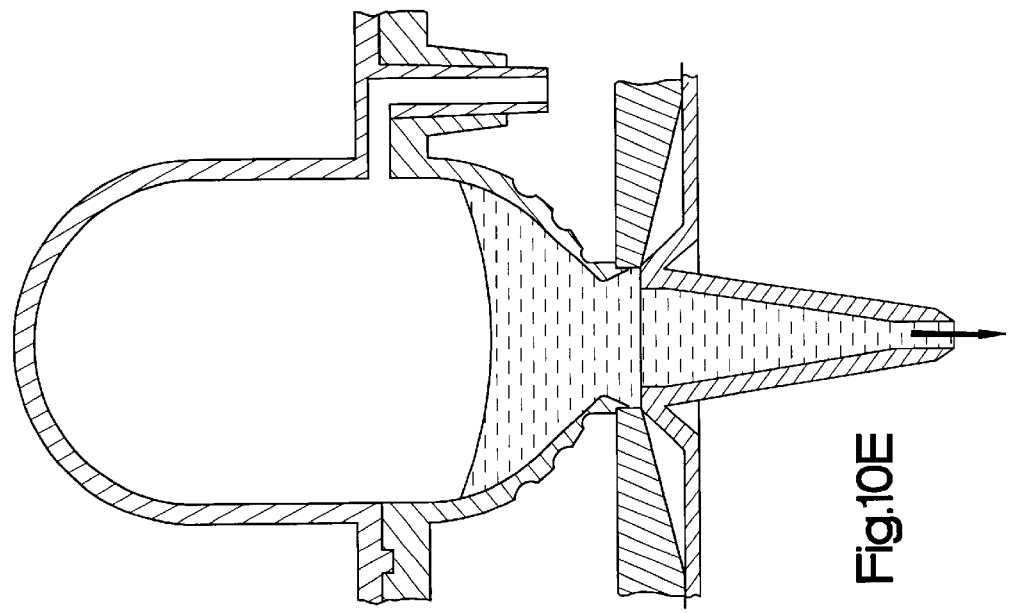

DEVICE FOR HANDLING SPECIMENS

This application is a division of U.S. patent application Ser. No. 09/180,356, filed Apr. 12, 1999, U.S. Pat. No. 6,350,414, which is a 371 of PCT/IL97/00141 filed May 1, 1997.

FIELD OF THE INVENTION

The present invention is generally in the field of laboratory handling of liquid specimens and more specifically concerns a multi-compartment plate capable of containing a plurality of liquid specimens and a method and system utilizing same.

BACKGROUND OF THE INVENTION

Processing of liquid specimens to test a variety of parameters therein, is a standard endeavor in research as well as in day-to-day clinical diagnostics. In order to reduce costs and increase efficiency of such method, improved accuracy and eliminate sources for error, there is a growing tendency to develop and use automated systems in which a plurality of liquid specimens are simultaneously handled. One device common in most such methods is a plate comprising a plurality of liquid holding compartments in which the liquid specimens may be incubated.

A variety of methods involve filtering of the specimen through a filter medium, a medium following incubation, in order to view the retentate remaining on the filter. Prior art devices allowing simultaneous incubation and subsequent simultaneous filtration of a plurality of liquid specimens are multi-compartment plates where the bottom wall of the compartments is constituted by a filter. Such is the case, for example, in the device disclosed in U.S. Pat. Nos. 4,493,815; 5,047,215 and 5,223,133. The filter for which such an application has a small pore size, does not readily enable seepage of liquid therethrough and only upon the application of a vacuum, the liquid is forced to flow through the filter. However, there is always some absorbance of liquid specimen onto the filter sheet, which may be significant in case of small specimens. In addition, in long incubation processes, in particular in such involving agitation of the specimens, there may also be some leakage of liquid through the filters even without the application of the vacuum.

In devices where the filter is permanently attached to the bottom wall of the compartment, there is an inherent difficulty in viewing the retentate, as this has to be through the opening of the compartment, by the use of long field optics.

When using a filter medium removable from the bottom wall, there is a very serious problem of ensuring a firm, leakage-proof attachment of the filter to the bottom of the compartments, which is a difficult feat to achieve simultaneously for all the compartments in a plate.

SUMMARY OF THE INVENTION

The present invention has, as one its objects, the provision of a novel device for simultaneous handling of a plurality of liquid specimens. It is particularly the object of the invention to provide such a device useful in procedures requiring filtration of the liquid specimens following incubation or any other treatment of the specimen within the compartment.

It is another object of the invention to provide a novel method for the simultaneous treatment of a plurality of liquid specimens and then filtering the specimens through a filter sheet for subsequent viewing of the retentate on the filter.

It is a further object of the invention to provide a novel system for simultaneous treatment of a plurality of liquid specimens and subsequent filtration of the specimens through a filter sheet.

Other objects of the invention will be clarified from reading of the following text.

The present invention provides, by a first of its aspects, a device in the form of a plate comprising a plurality of compartments, each compartment being adapted to hold a liquid specimen and having an aperture at its top for introducing and withdrawing liquid into and from the compartment, respectively; each compartment has a vent opening at a side wall at about mid portion thereof between the compartment's top and bottom.

The present invention provides a filter device for filtering specimens contained in a multi-compartmental plate comprising a planar body with a top and bottom face, having a plurality of openings, and a filter sheet stretched to cover all openings, the device being attachable to said plate at its top face with each opening being in register with and attached to an aperture of one compartment, such that the filter is stretched over said aperture to allow vacuum filtration of specimens from the compartments through the filter.

In accordance with a preferred embodiment, the filter sheet is stretched over said bottom face. In accordance with another preferred embodiment, said filter device cooperates with a support member attached to the bottom face of the filter device for supporting the filter during the vacuum filtration. Typically, the filter sheet is stretched by cooperation stretching members in such filter device and in said support member, e.g. projections in one and recesses in the other for receiving the projections.

In accordance with another aspect of the invention there is provided a method for processing a plurality of liquid specimens, comprising:

a) providing a multi-compartmental plate which comprises a plurality of compartments each adapted to hold a liquid specimen and having an aperture at its top for introducing or removing of liquid and a vent opening within the compartment at a mid-portion thereof;

b) introducing each one of the plurality of liquid specimens into one of the plate's compartments;

c) treating or incubating the specimens contained in the compartments;

d) attaching a filter sheet to the plate such that it covers the openings of the compartments and propelling the liquid through the filter sheet; and e) separating the filter sheet from the plate and viewing particulate retentate remaining on the filter sheet.

A further aspect of the present invention is concerned with a system for simultaneous processing of a plurality of liquid specimens, comprising:

i. a multi-compartmental plate as defined above;

ii: a filtration assembly comprising a filter device as defined above, and preferably also said support device.

A unique feature of the multi-compartmental plate, the method or system of the invention is in that the filter sheet is attached to the plate only at the end of the specimen's treatment process, just prior to filtration. Thus, in accordance with the invention there is no contact between the filter sheet and the liquid specimen until that stage.

A particular preferred application of the invention is in the field of assaying liquid specimens, both in research and in clinical diagnostics, in order to qualify or quantify the presence, type of characteristics of living matter contained therein, e.g. to diagnose microorganismal infection in a body fluid.

The invention will now be illustrated, by way of example only, by some non-limiting specific embodiments, with reference to the annexed drawings.

BRIEF DESCRIPTION OF THE DRAWINGS

FIG. 3A is a cross-sectional view, taken along lines III—III in FIG. 1, showing the two members which are joined together to form the multi-compartmental plate;

FIG. 3B is an exploded view of FIG. 3A showing the two constituents of the plate;

FIGS. 10(A–G) shows the sequence of operation of using a multi-compartmental plate of the invention, represented here by a single compartment.

FIG. 10A shows the compartment prior to inoculation of a specimen;

FIG. 10B shows an empty compartment during specimen and reagent inoculation.

FIG. 10C shows the compartment after attachment of the filtration assembly;

FIG. 10D shows the compartment after inversion and prior to application of a vacuum;

FIG. 10E shows the compartment during the vacuum application stage;

FIG. 10F shows an empty compartment after complete withdrawal of the liquid with a retentate remaining on the filter sheet;

DESCRIPTION OF THE EMBODIMENTS

Figure 1:
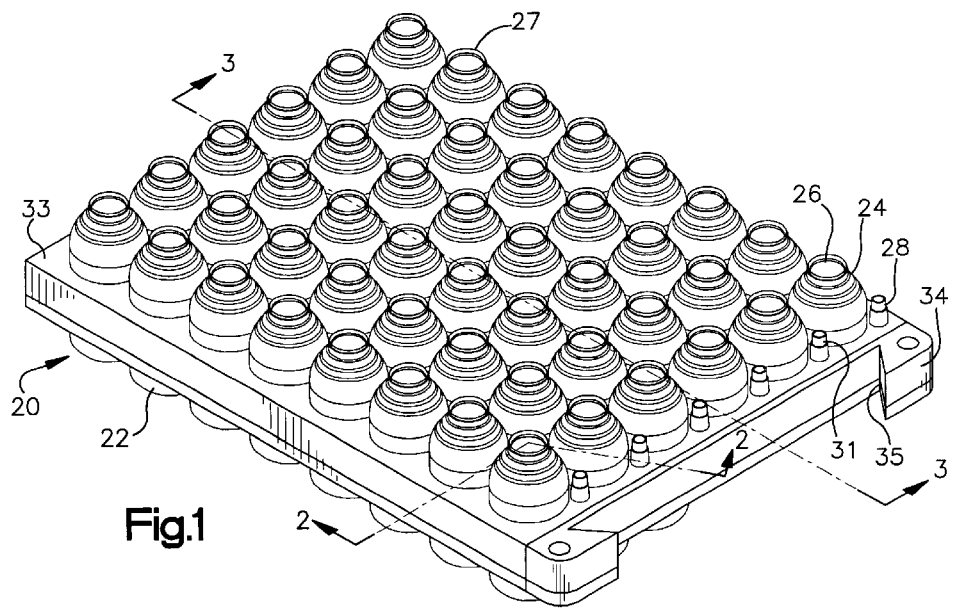
FIG. 1 is an isometric view of a multi-compartmental plate in accordance with an embodiment of the invention.
Figure 2:
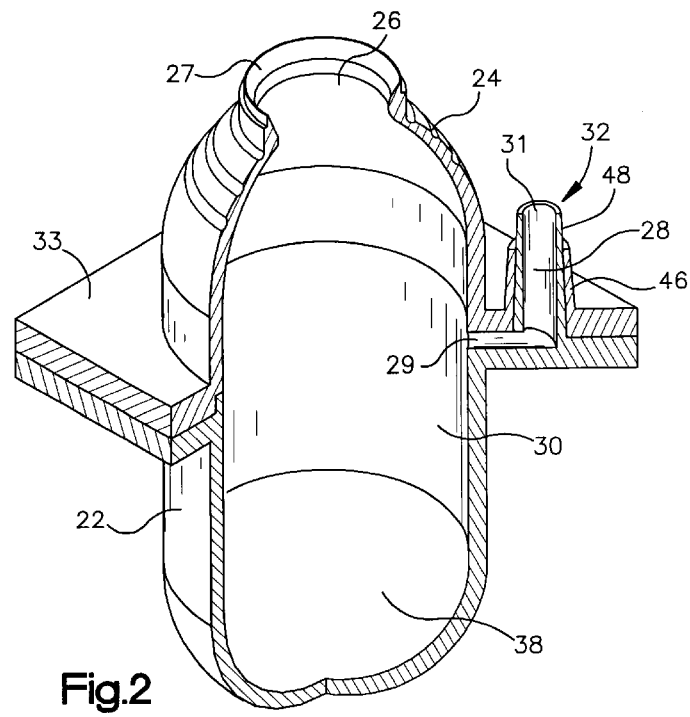
FIG. 2 is a partial isometric cross-sectional view of a single compartment taken along line II—II in FIG. 1.

Reference is first being made to FIGS. 1–3 showing a multi-comparbiental plate in accordance with the invention. The plate generally designated 20 has a plurality of compartments 22, adapted to hold liquid, each having upper diverging portion 24 ending in an aperture 26 having an annular rim 27. Each of compartments 22 has an associated L-shaped venting duct 28 having an opening 29 at a midportion 30 of the compartment and another opening 31 at the end of an upright direct portion 32 projecting upwards from the top face 33 of the plate. As can be seen particularly in FIG. 2, the bottom portion 38 of the compartment has an inverted dome-shape.

The plate has a circumferencial frame 34 with a dovetailing engaging member 35 adapted to be engaged by an appropriate member of a manipulation (not shown).

As can be seen particularly in FIG. 3, plate 20 is assembled from an upper member 42 and a lower member 44 which are typically combined by ultrasonic welding. As can further be seen, the upper member has a plurality of bosses 46 which are adapted to accommodate duct-defining projection 48 both of which form together projection 32.

Figure 4:
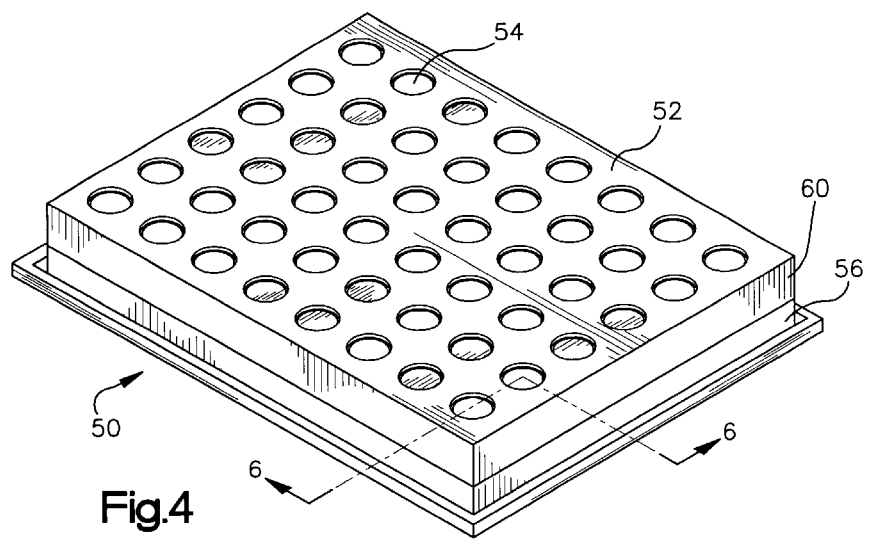
FIG. 4 is an isometric view of a filtering assembly, in accordance with an embodiment of the invention, for use in conjunction with the multi-compartmental plate of FIG. 1.
Figure 6:
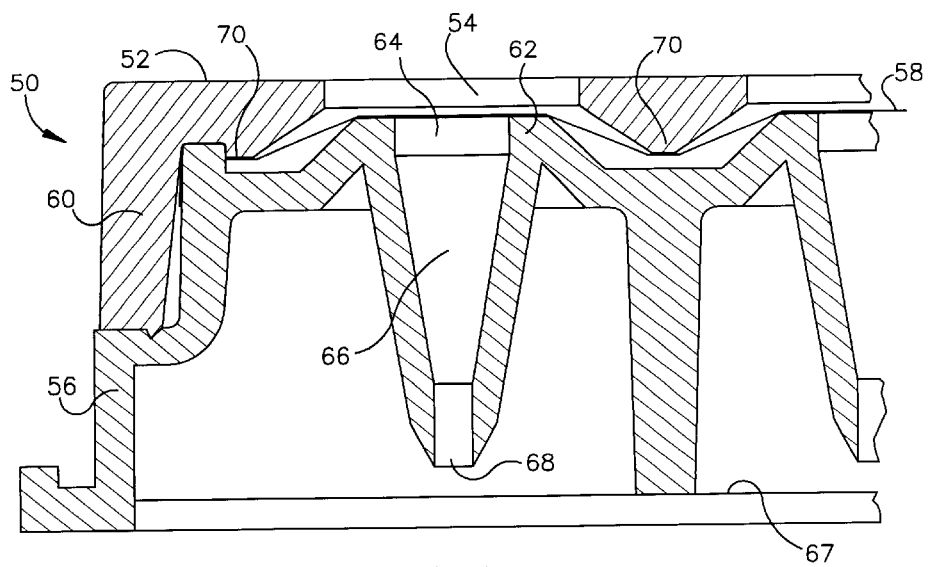
FIG. 6 is a cross-section through line VI—VI in FIG. 4.
Figure 5:
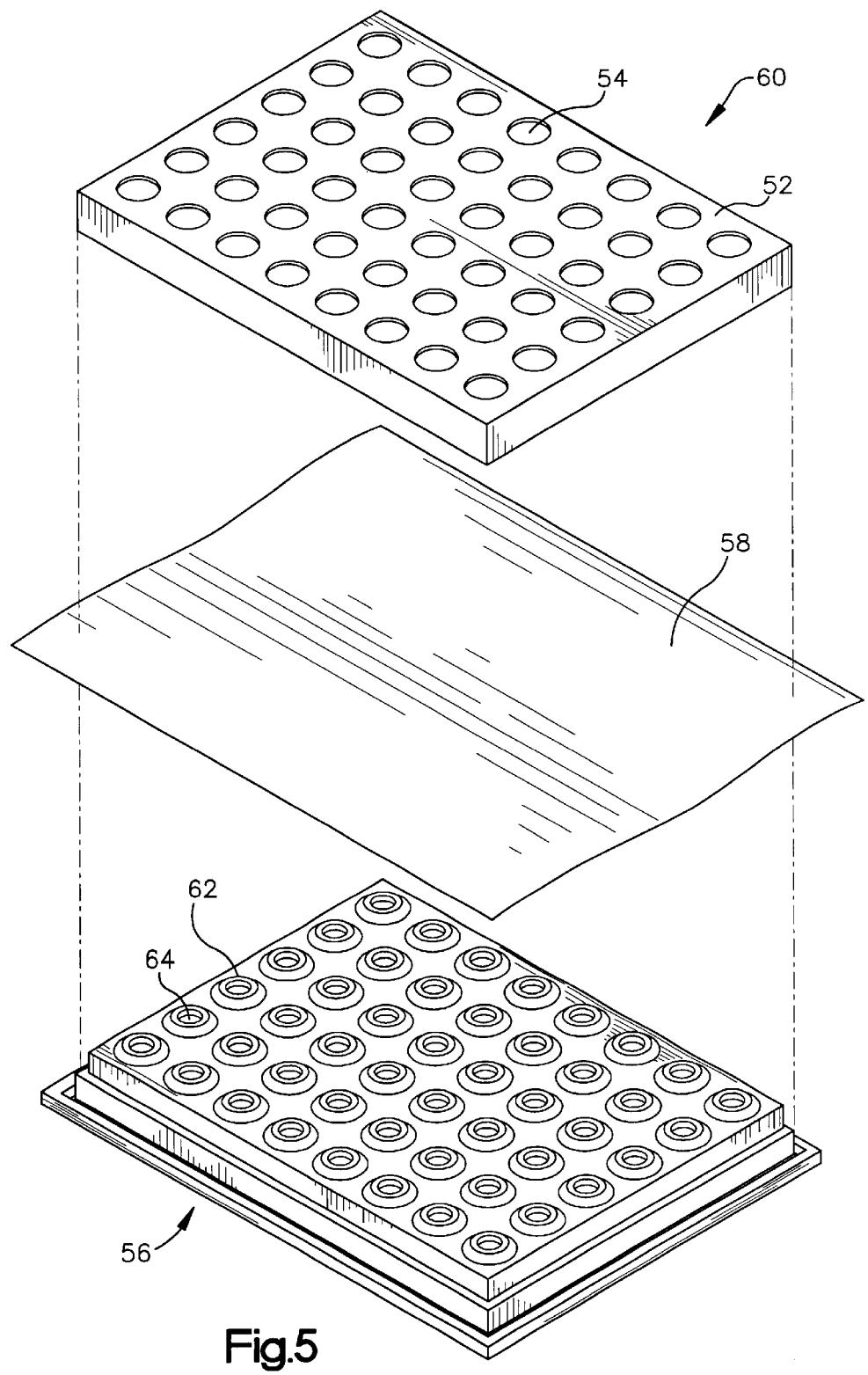
FIG. 5 is an exploded isometric view showing the three constituents of the filtering assembly.

FIGS. 4, 5 and 6, show the filtering assembly 50 having an upper face 52 comprising a plurality of openings 54 each of which corresponding to and adapted to receive on aperture 26 of compartment 22. With particular reference to FIG. 5, it can be seen that filtering assembly 50 is assembled from a base, bottom member 56, a filter sheet 58 and a filter retaining and stretching, upper member 60. Base member 56 comprises a plurality of annular projections 62 with openings 64. Openings 64 are the upper ends of converging ducts 66 ending towards a bottom face 67 of member 56 with a bottom opening 68. As can further be seen in FIG. 6, member 60 has a plurality of downward projections 70 interposed between openings 54.

Once the three components of assembly 50 are assembled together, filter sheet 58 is tensioned over opening 64 by the combined action of annular projection 62 and downward projection 70, ensuring a tight, leakage proof fit between filter sheet 58 and opening 64.

Figure 7:
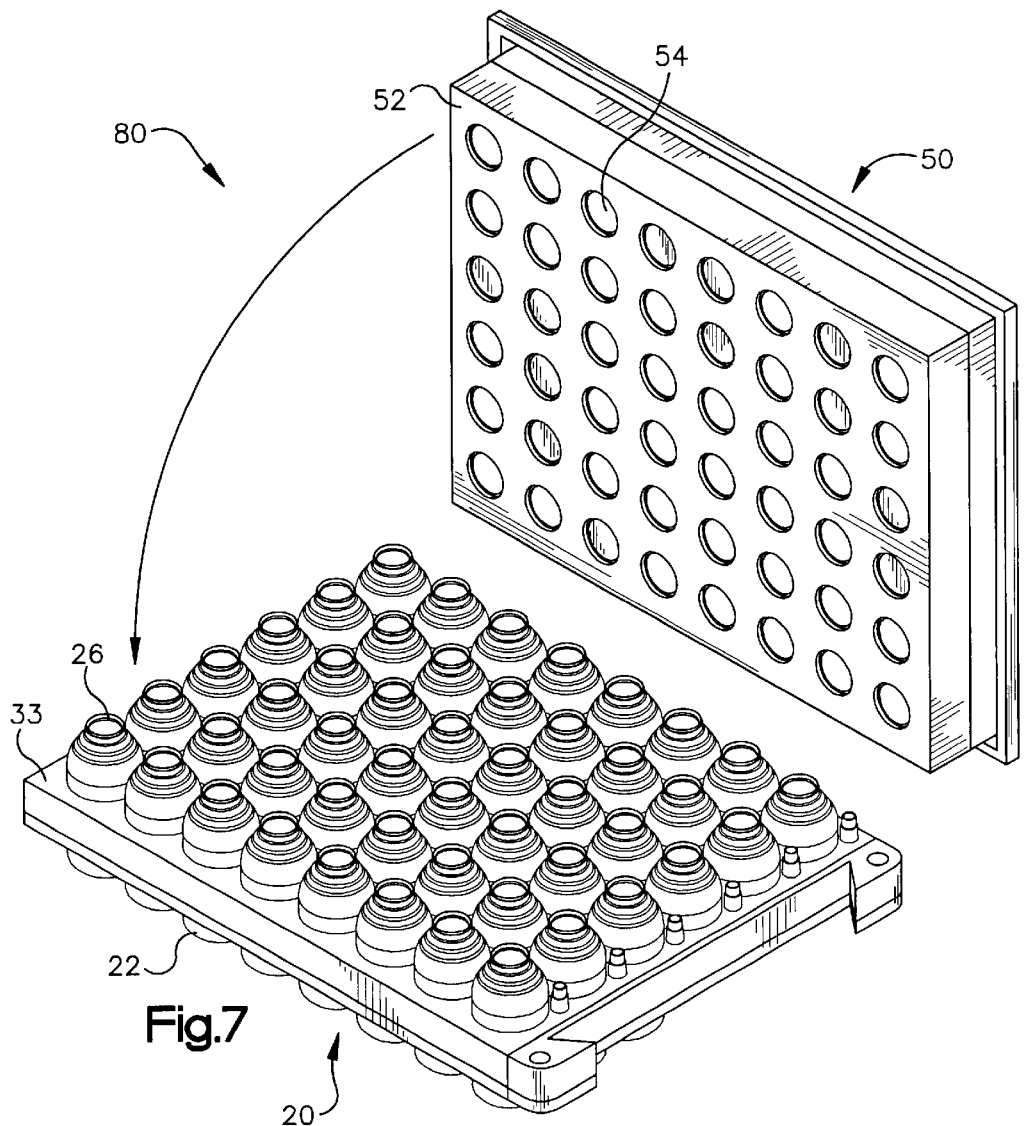
FIG. 7 is an isometric view of the multi-compartmental plate and the filtration assembly during their attachment to one another for filtration of the liquid specimen contained in the compartments of the multi-compartmental plate.
Figure 8:
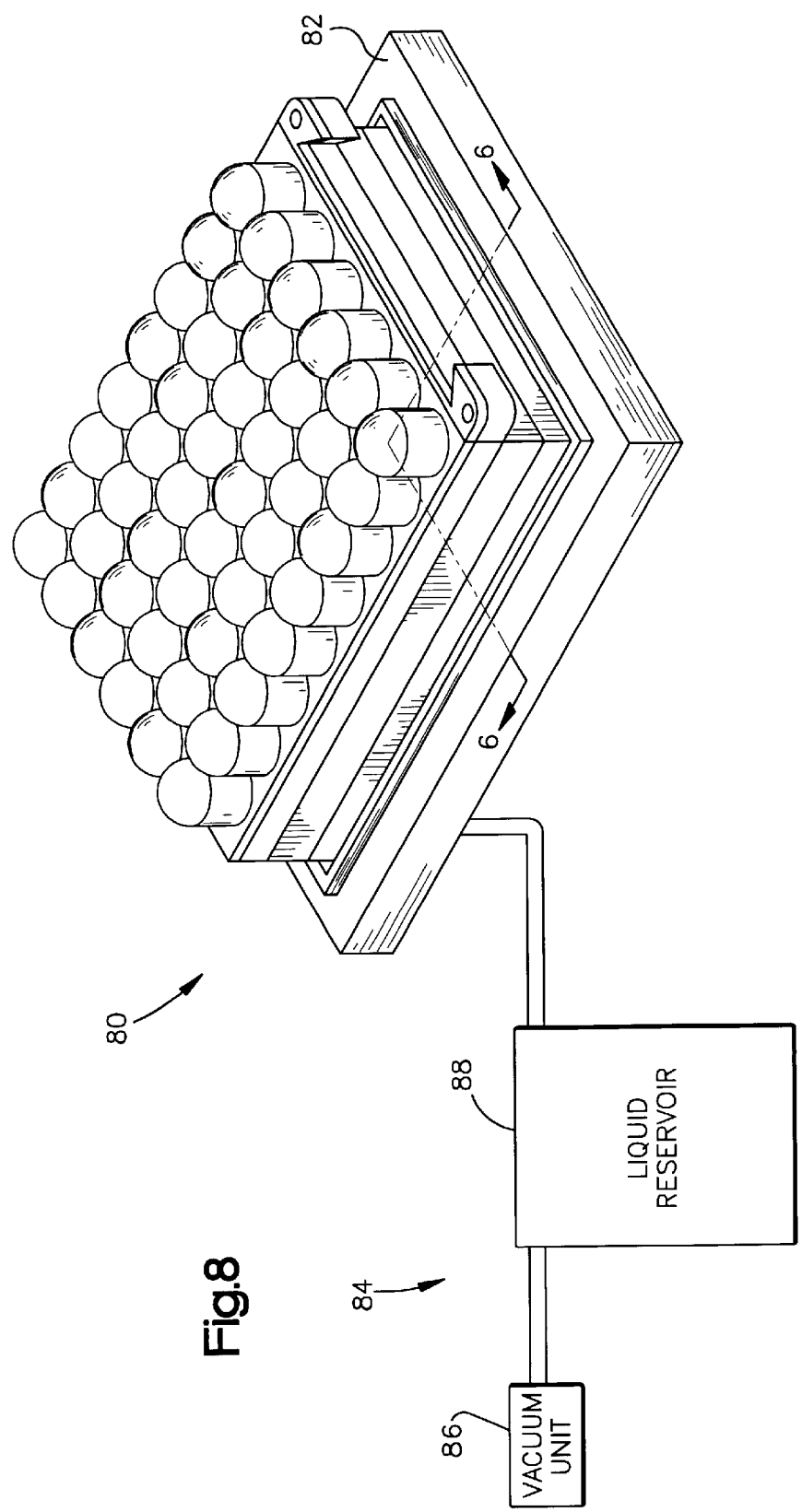
FIG. 8 is an isometric view showing all the components together on a vacuum stage during filtration.
Figure 9:
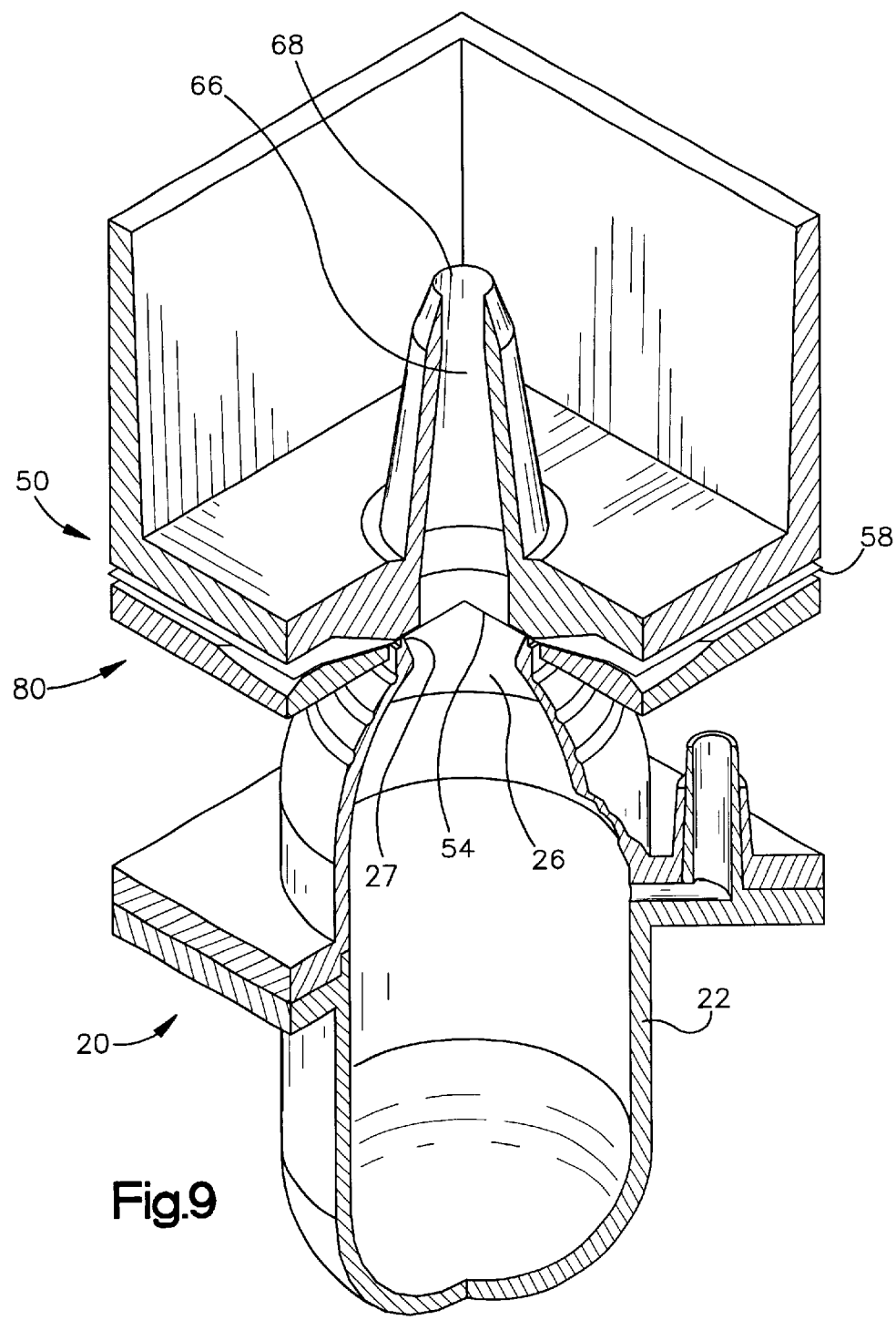
FIG. 9 is a cross-section through line IX—IX in FIG. 8 during the filtration process (without the vacuum stage) in an upright position (with the filtration assembly on top of the plate)

With reference now to FIG. 7, it can be seen that for filtration of liquid specimens contained in the compartments 22 of plate 20, the filtration assembly 50 is turned upside down and its upper face 52 is attached to the upper face 33 of plate 20. Each of openings 54 of plate 50 correspond to and are in register with aperture 26 in plate 20. Once engaged, the entire assembly 80 consisting of plate 20 and filter assembly 50 is inverted and can be placed on a vacuum stage 82, as can be seen in FIG. 8. Vacuum stage 82 is connected to a vacuum system 84 consisting of a vacuum unit 86 and a liquid disposing reservoir 88. With reference to FIG. 9, it can be seen that at this state the annular rim 27 is snugly held within opening 54 and aperture 26 tightly engages filter sheet 58 and consequently, once the vacuum is applied, a liquid specimen contained in compartment 22 is drawn through the filter sheet 58 and through duct 66, via outlet 68 to the liquid reservoir 88.

Figure 10G:
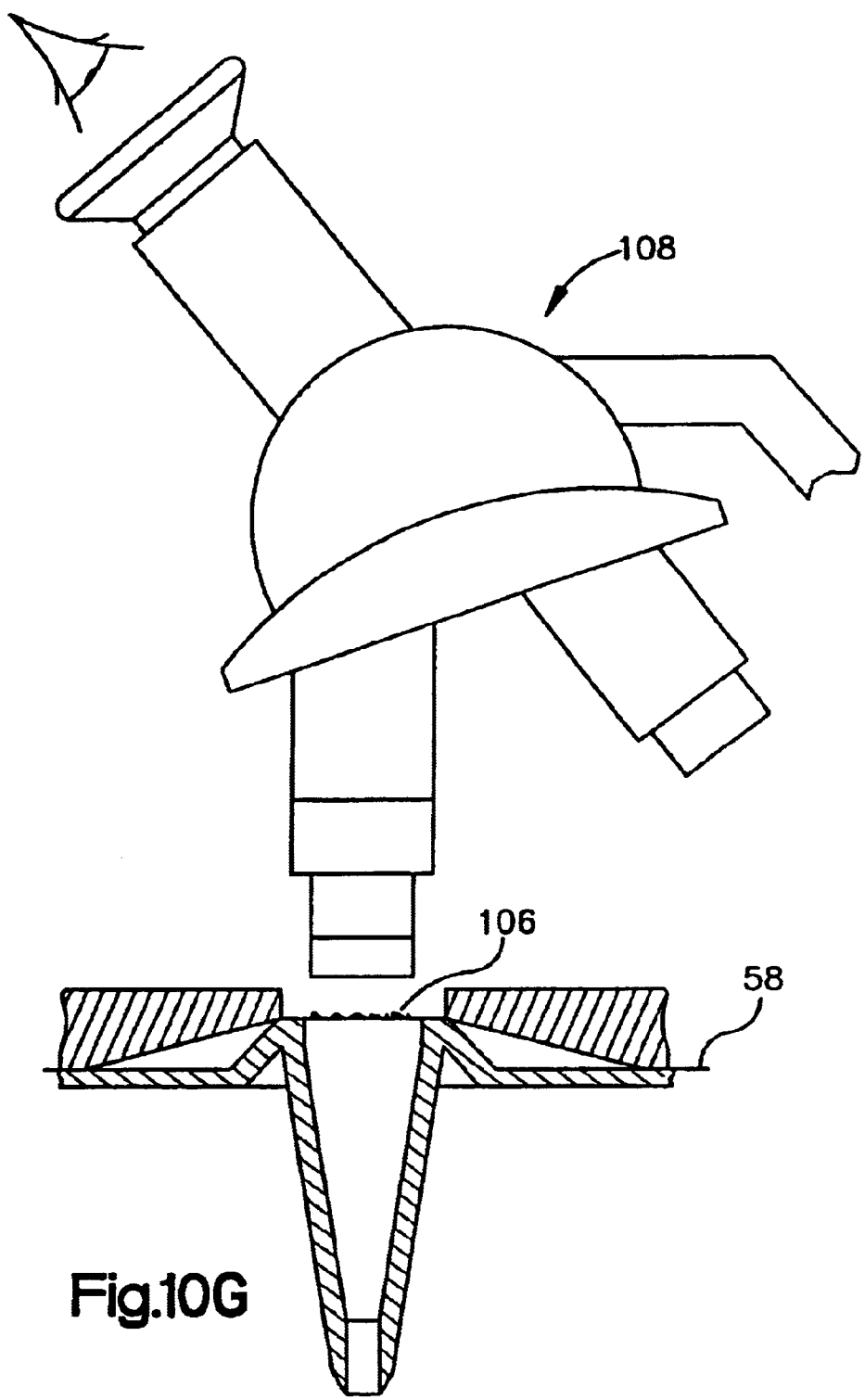
FIG. 10G shows the step of inspection of the retentate of the filter sheet.

A sequence of operation in a system of the invention can be seen in FIGS. 10A–10G. At an initial stage (FIG. 10A) the multi-compartmental plate is held with the aperture 26 of each of the compartments facing upwards, allowing inoculation of liquid specimens 100 and optionally a reagent solution 102, by means of a suitable pipettor 104 (FIG. 10B). Following incubation, the multi-compartmental plate 20 is engaged with the filtering assembly 50 (FIG. 10C), as explained above, (FIG. 10C) and this entire assembly 80 is then inverted (FIG. 10D). Then following application of a vacuum, liquid is drawn through the filter (FIG. 10E), as already explained above, and after emptying of the compartment, the particulate matter 106 contained in the specimen is retained on sheet 58 (FIG. 10F). Finally, plate 20 can be removed and discarded and the filtration assembly can then be taken as is for viewing of the retentate 106 by a microscope 108, optionally forming part of a computerized image only in system (not shown).

Figure 11:
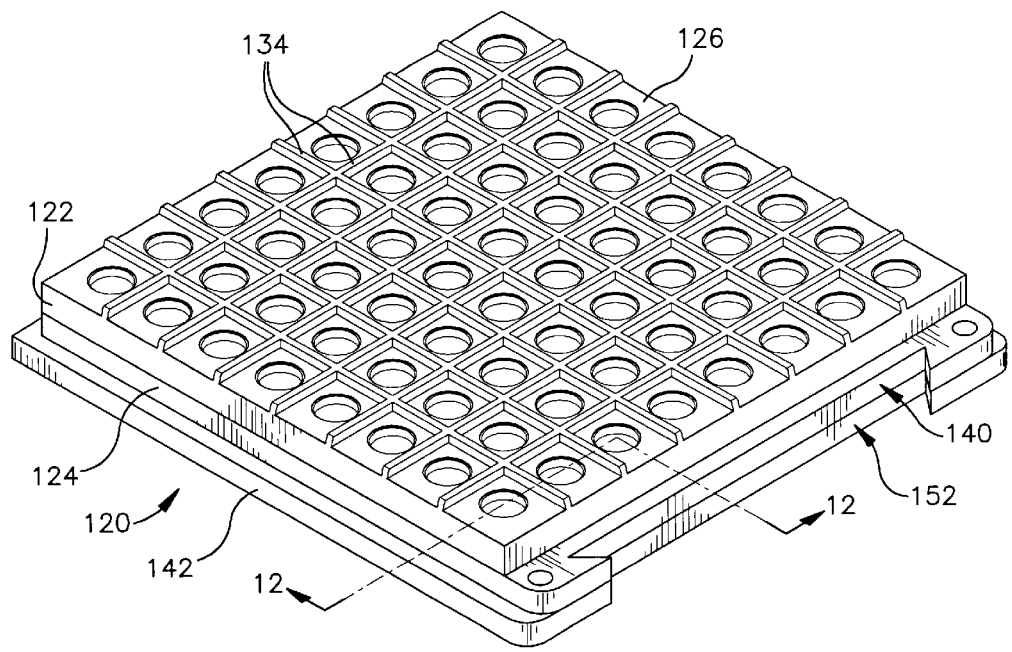
FIG. 11 is an isometric view of a filtration assembly in accordance with another embodiment of the invention, comprising independent filter device and support body.
Figure 12:
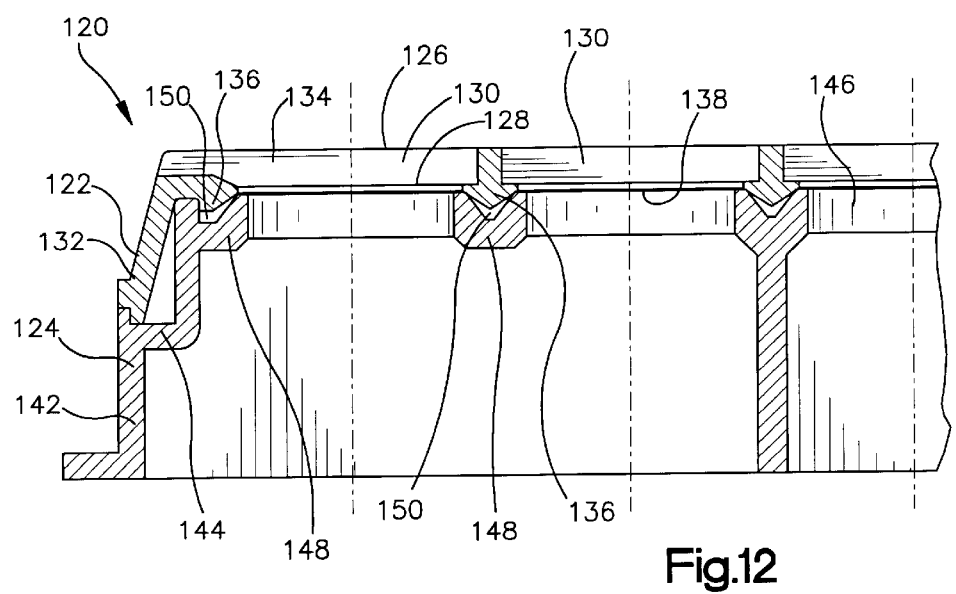
FIG. 12 is a partial cross-sectional view along the lines XII—XII in FIG. 11.
Figure 13:
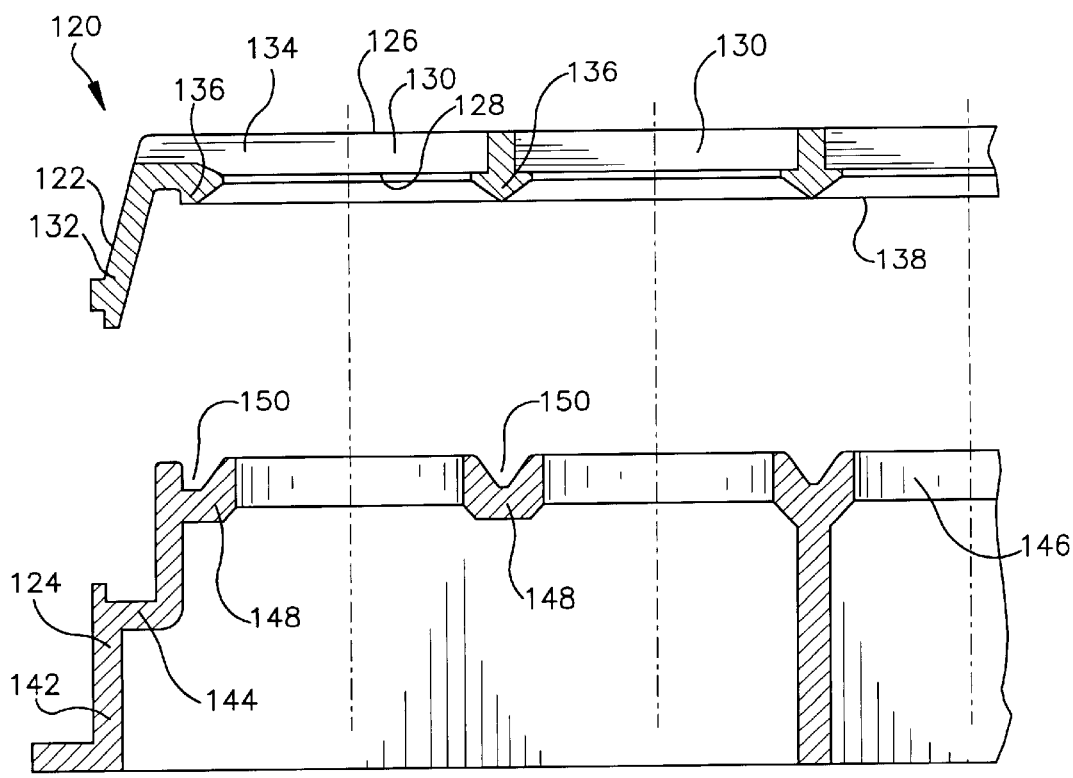
FIG. 13 is a partial, exploded cross-sectional view along the lines XII—XII in FIG. 11.

Reference is now being made to FIGS. 11–13 relating to an embodiment of a filtering assembly 120, which unlike filtering assembly 60, comprises two individual, separable components, namely filter device 122 and filter support member 124. Filter device 122 is generally a planar member with a top face 126 and a bottom face 128 with a plurality of openings 130. Filter device 122 has a peripheral skirt 132 upward projecting reinforcing ribs 134 and downward tensioning projections 136. Filter 138 is stretched between edges of the device 122 and attached to the edges of the device 122 by ultrasonic welding, gluing, etc. Device 122 further comprises a dovetail engagement portion 140, to allow manipulation of the device by a robotic arm.

Filter support member 124 has a frame 142 with a shoulder 144 adapted to receive and fit with skirt 132 of filter device 122. Device 124 has a plurality of openings 146, each one formed between a pair of ribs 148, each of which has an indention 150 for receiving downward projections 136 of device 122. Filter support member in the embodiment shown has also a dovetail engagement portion 152.

Filter 128 is initially retained and stretched between the edges of device 122, as can be seen in FIG. 13. Once the two devices, namely filter device 122, as can be seen in FIG. 13. Once the two devices, namely filter device 122 and filter support member 124 are attached to one another, as shown in FIG. 12, the filter becomes stretched over ribs 148. Typically, device 122 will first be attached to multi-compartmental plate at its top face 126, and then the two together will be attached to filter support member 124, so as to form the filtration assembly. Alternatively, the two components of the filtration assembly, namely devices 122, 124 may first be attached to one another and then both of them together will be attached to a multi-coompartmental plate. For viewing of the particulate retentate remaining on the filter, filter device 122 is detached from filter supported member 124 and brought to a microscope similarly as the filter assembly as shown in FIG. 10G.

A particular preferred implementation of a multi-compartmental plate and the above described system is in processing of biological liquid specimens, e.g. urine specimens. In accordance with this preferred embodiment, the liquid specimen is incubated for a time to allow cells to multiply and increase their number, for a time sufficient to allow absorption of a dye into the cells, etc. Then after filtration, as described above, the cellular material retained on filter sheets can be viewed, characterized or counted. The viewing of the retained matter is preferably by means of an automated image analysis system.

Viewing of the retentate can, for example, be by means of epifluorescence. However, it is possible also, to use bottom elimination.

In addition to processing and using particulate matter, the plate and system of the invention may be used also for a variety of other applications, e.g. analysis of crystals formed following a chemical reaction in the liquid specimen.

Preferably, all the components of the system are disposable, although they can also be made to be suitable for reuse, after sterilization.

While the entire system may be used manually, a particularly preferred implementation of the system is for automatic, robot utilizing, processing system.

What is claimed is:

1. An apparatus comprising:
   an array of liquid specimen containers having open upper ends;
   a panel structure having an array of openings and configured for each opening to be aligned with a corresponding one of said open upper ends upon engagement of said panel structure with said containers; and
   filter material mounted on said panel structure in a condition stretched across said openings so as to extend across said open upper ends upon said engagement, such that liquid contents of said containers can flow downward through said filter material when said containers are overturned while maintaining said engagement.

2. An apparatus as defined in claim 1 wherein said filter material is a single filter sheet.

3. An apparatus as defined in claim 1 wherein said filter material is fixed to said panel structure.

4. An apparatus as defined in claim 1 wherein said panel structure is configured for said open upper ends to extend into said openings upon said engagement.

5. An apparatus comprising:
   a liquid specimen container having an open upper end;
   a panel structure having an opening and configured for said opening to register with said open upper end upon engagement of said panel structure with said container; and
   filter material mounted on said panel structure in a condition stretched across said opening so as to extend across said open upper end upon said engagement, such that liquid contents of said container can flow downward through said filter material when said container is overturned while maintaining said engagement.

6. An apparatus as defined in claim 5 wherein said container is one of an array of liquid specimen containers, each container having an open upper end, and said opening is one of an array of openings configured for each opening to register with a corresponding one of said open upper ends upon said engagement.

7. An apparatus as defined in claim 5 wherein said filter material is a single filter sheet.

8. An apparatus as defined in claim 5 wherein said filter material is fixed to said panel structure.

9. An apparatus as defined in claim 5 wherein said panel structure is configured for said open upper end to extend into said opening upon said engagement.

10. An apparatus comprising:
    an array of liquid specimen containers having open upper ends;
    a panel structure having an array of openings and configured for each opening to be aligned with a corresponding one of said open upper ends upon engagement of said panel structure with said containers; and
    filter material stretched across said openings so as to extend across said open upper ends upon said engagement, such that liquid contents of said containers can flow downward through said filter material when said containers are overturned while maintaining said engagement;
    wherein said panel structure includes a first panel with said openings, and a second panel with openings aligned with said openings in said first panel, and said filter material is located between said first and second panels.

11. An apparatus as defined in claim 10 wherein said second panel has duct structures projecting from said openings in said second panel and away from said openings in said first panel.

12. An apparatus as defined in claim 10 wherein said first panel has projections engaging and stretching said filter material toward said second panel.

13. An apparatus as defined in claim 12 wherein said second panel has indentations in which said projections are received.

14. An apparatus as defined in claim 10 wherein said second panel has projections engaging and stretching said filter material toward said first panel.

15. An apparatus comprising:

a liquid specimen container having an open upper end;

a panel structure having an opening and configured for said opening to register with said open upper end upon engagement of said panel structure with said container; and filter material stretched across said opening so as to extend across said open upper end upon said engagement, such that liquid contents of said container can flow downward through said filter material when said container is overturned while maintaining said engagement;

wherein said panel structure includes a first panel having said opening, and further includes a second panel having an opening aligned with said opening in said first panel, and said filter material is located between said first and second panels.

16. An apparatus as defined in claim 15 wherein said second panel has a duct structure projecting from said opening in said second panel and away from said opening in said first panel.

17. An apparatus as defined in claim 15 wherein said first panel has a projection engaging and stretching said filter material toward said second panel.

18. An apparatus as defined in claim 17 wherein said second panel has an indentation in which said projection is received.

19. An apparatus as defined in claim 15 wherein said second panel has a projection engaging and stretching said filter material toward said first panel.

20. An apparatus as defined in claim 19 wherein said projection on said second panel is an annular structure surrounding said opening in said second panel.

* * * * *